Figure 1:
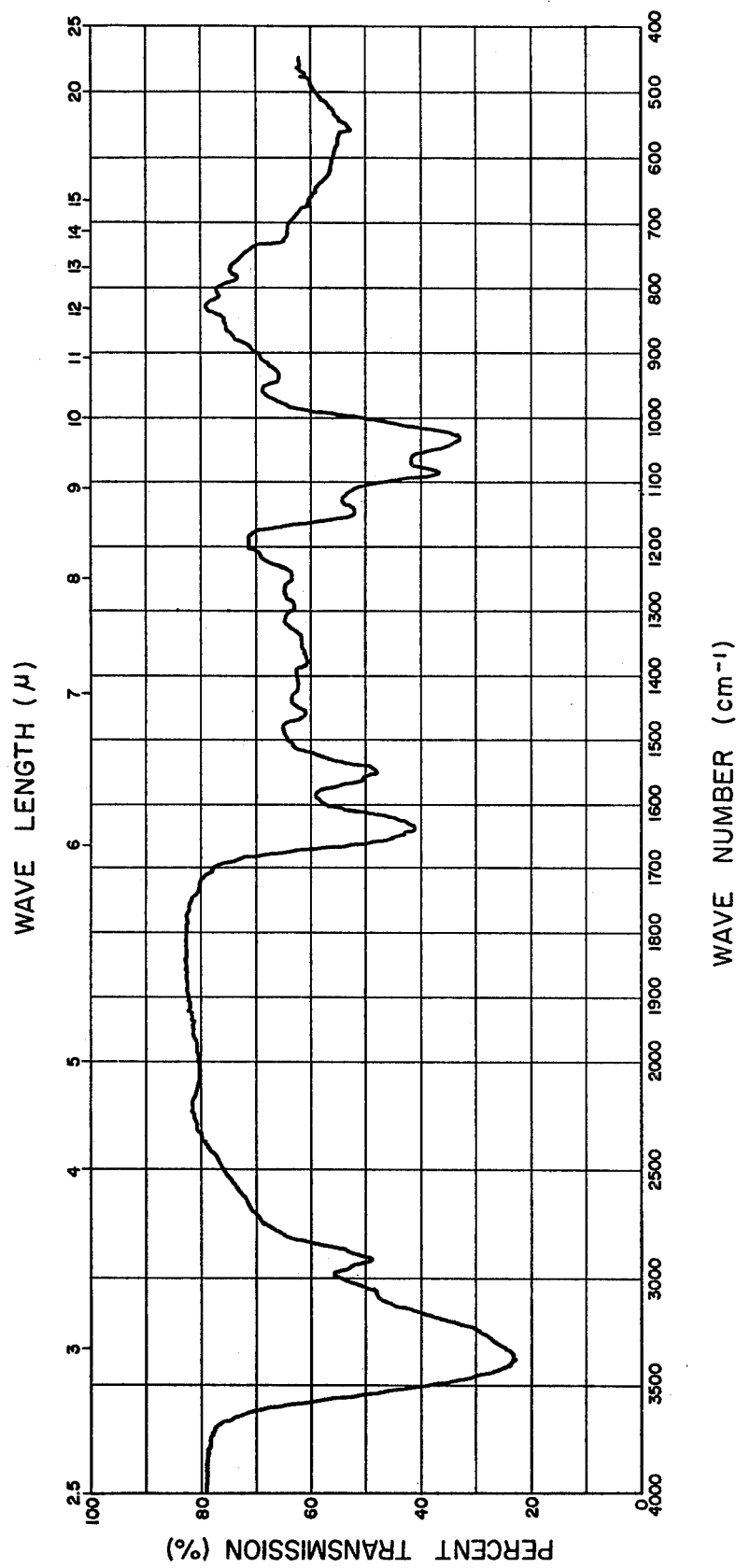

United States Patent [19]

Nara et al.

[11] 4,108,724
[45] Aug. 22, 1978

[54] METHOD FOR PREPARING ANTIBIOTIC P-2563 USING *PSEUDOMONAS FLUORESCENS*

[75] Inventors: Kiyoshi Nara, Kyoto; Yasuhiro Sumino, Kobe; Mitsuko Asai, Takatsuki; Shunichi Akiyama, Suita, all of Japan

[73] Assignee: Takeda Chemical Industries, Ltd., Japan

[21] Appl. No.: 674,310

[22] Filed: Apr. 7, 1976

[30] Foreign Application Priority Data

Apr. 11, 1978 [GB] United Kingdom ............... 15062/75

[51] Int. Cl.$^2$ .................................................. C12D 9/20
[52] U.S. Cl. .................................................... 195/96
[58] Field of Search ........................... 536/17; 195/96

[56] References Cited

U.S. PATENT DOCUMENTS

| 3,977,943 | 8/1976 | Barrow et al. ............. 195/96 |
| 4,012,576 | 3/1977 | Kawaguchi et al. ......... 195/96 X |

OTHER PUBLICATIONS

Amano et al., "New Antibiotic BN68", Chemical Abstracts vol. 83, No. 25, (1975), p. 278 abs. No. 204760w.
Kiprianova et al., "Pigments of Fluorescent Bacteria from the Genus Pseudomonas and Their Antibiotic Properties", Chemical Abstracts, vol. 74, (1971), No. 25, p. 162, abs. No. 136745g.
Ito et al., "New Antibiotics Produced by Bacteria Grown on N-paraffins (Mixture of $C_{12}$, $C_{13}$ and $C_{14}$ fractions)", Chemical Abstracts, vol. 74, (1971), No. 11, p. 221, abs. No. 52093e.
Reddi et al., "Antibiotic Properties of 2,4-Diacetylphloroglycinol [2,4-Diacetyl-1,3,5-Trihydroxybenzene] Produced by Pseudomonas Fluorescens 26-0," Chemical Abstracts, vol. 72, (1970), No. 13, p. 119, abs. No. 63915j.

*Primary Examiner*—Raymond N. Jones
*Assistant Examiner*—Thomas G. Wiseman
*Attorney, Agent, or Firm*—Wenderoth, Lind & Ponack

[57] ABSTRACT

A novel antibiotic P-2563 is produced by cultivating a microorganism of the genus Pseudomonas.

The antibiotic is useful as a drug for the treatment of pustule, and also useful as a disinfectant.

5 Claims, 12 Drawing Figures

METHOD FOR PREPARING ANTIBIOTIC P-2563 USING *PSEUDOMONAS FLUORESCENS*

This invention relates to a new antibiotic herein designated as Antibiotic P-2563 and to a method for producing this antibiotic.

It has been found by the present inventors that a novel antibiotic is accumulated by a microorganism belonging to the genus Pseudomonas in the culture broth; that the new antibiotic is useful as a drug for the treatment of pustule and other diseases, and also used for disinfecting apparatuses, instruments and equipment. The new antibiotic has been named as "Antibiotic P-2563".

The antibiotic P-2563 is designated by the following general formula,

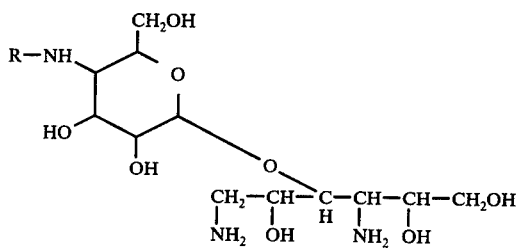

wherein R stands for hydrogen or an acyl group.

Referring to the above general formula, the acyl group has one to 7 carbon atoms and is exemplified by formyl, acetyl, propionyl, butyryl, isobutyryl, valeryl, isovaleryl hexanoyl, heptanoyl and so on and preferably one which has one to 5 carbon atoms.

The antibiotic P-2563 has a dextrorotatory property.

The new antibiotic P-2563-producing microorganism which is employed herein according to this invention may be any strain belonging to the genus Pseudomonas which is able to elaborate and to accumulate the antibiotic P-2563. The strain *Pseudomonas fluorescens* P-2563, which we have isolated from a soil sample collected in the city of Kyoto, Japan, is one of the preferred microorganisms which can be employed according to this invention.

The microbiological characteristics and properties of the strain *Pseudomonas fluorescens* P-2563 (hereinafter referred to briefly as the P-2563 strain) are as follows:

(a) Morphological features (1) Cell configuration: Rod-shaped Dimensins of cell: 0.5–1 μ × 1–3 μ
(2) Pleomorphism: Non-pleomorphic
(3) Motility: Motile Mode of attachment of flagella: one or more flagellas per pole
(4) Sporogenicity: None-sporulating
(5) Gram's stain: Negative
(6) Acid-fastness: Negative (b) Cultural characteristics (grown at 28° C. for 3 to 7 days and investigated in the routine manner)

(1) Bouillon agar plate

The surface is smooth at initial stages of growth but becomes streaked gradually. Circular and flat or semi-lenticular, with an entire margin, homogenous and translucent. The wet gloss is opalescent with a tinge of yellow. No soluble pigment.

(2) Bouillon agar slant

Moderate growth, effused, flat, moist, smooth, translucent and opalescent with a tinge of yellow; viscous. No soluble pigment.

(3) Bouillon fluid

No surface growth, with slight turbidity. Tufted to viscous sediments.

No production of gas. The medium is not pigmented.

(4) Bouillon gelatin stab

Membranous growth on the surface, with sediments white with a tinge of brown. Stratiform liquefaction.

(5) Litmus milk

Coagulation at 37° C. At 28° C, partial coagulation and gradual peptonization occur. Weakly alkaline.

(c) Physiological properties (1) Reduction of nitrates: Positive
(2) Dentrification: Negative
(3) MR test: Doubtful positive.
(4) VP test: Negative
(5) Production of indole: Negative
(6) Production of hydrogen sulphide: Negative
(7) Hydrolysis of starch: Negative
(8) Utilisation of citric acid: Positive
(9) Utilisation of inorganic nitrogen sources: Positive
(10) Production of pigment: a water-soluble fluorescent pigment (on King B medium)
(11) Urease: Negative
(12) Oxidase: Positive
(13) Catalase: Positive
(14) Growth ranges: Temperature: 4° C to 37° C. pH : 4.5 to 9.5
(15) Attitude toward oxygen: Aerobic
(16) O-F test (High-Leifson's method): oxidised.
(17) Production of acid and gas from various carbohydrates:

The spectrum of acid and gas production from various carbohydrates is shown in Table 1 below.

Table 1

| No. | Carbohydrate | Production of acid | Production of gas |
|---|---|---|---|
| 1 | L-arabinose | + | − |
| 2 | D-xylose | + | − |
| 3 | D-glucose | + | − |
| 4 | D-mannose | + | − |
| 5 | D-fructose | + | − |
| 6 | D-galactose | + | − |
| 7 | Maltose | − | − |
| 8 | Sucrose | − | − |
| 9 | Lactose | − | − |
| 10 | Trehalose | − | − |
| 11 | D-sorbitol | − | − |
| 12 | D-mannitol | − | − |
| 13 | Inositol | − | − |
| 14 | Glycerin | − | − |
| 15 | Starch | − | − |

Reference of the above observations to the descriptions in Bergey's Manual of Determinative Bacteriology (7th ed.) indicates that the present strain is a strain of *Pseudomonas fluorescens.*

The strain has been deposited at the Fermentation Research Institute, the Agency of Industria Science and Technology, Chiba, Japan under the accession number FERM-P No. 2894; at the Institute for Fermentation, Osaka, Japan under the ascertain number under IFO 13658, and at the American Type Culture Collection, U.S.A. under the accession number: ATCC 31125.

The strain of *Pseudomonas fluorescens* which is thus employed in the practice of this invention is liable to variations in characteristics as are other Pseudomonas strains, and can be easily induced to undergo variation and mutation by varied artificial means such as, for example, irradiation with ultraviolet light or X-rays, or by means of a chemical mutagen. It should be understood that, irrespective of what mutant it is or in what manner it has been induced, any such mutant can be invariably employed for the purposes of this invention only if it is able to produce the antibiotic P-2563 herein contemplated.

In accordance with this invention, such a P-2563-producer of the genus Pseudomonas is cultivated in a medium containing such nutrients as are ordinarily utilized by microorganisms. Thus, as carbon sources, there may be employed, among others, carbohydrates (e.g. starch, glucose, sucrose, etc.), alcohols (e.g. glycerin, methanol, ethanol, butanol, etc.), fatty acids (e.g. acetic acid, propionic acid, linoleic acid, stearic acid, etc.), oils and fats (e.g. soyabean oil, olive oil, fish oil, sperm oil, cotton seed oil, palm oil, etc.), n-paraffins (e.g. decane, hexadecane, pentacosane, etc.) and other hydrocarbons (e.g. kerosene, gas oil, etc.). As nitrogen sources, there may be employed various organic and inorganic nitrogen sources such as peptone, soybean flour, cotton seed flour, corn steep liquor, wheat germs, dried yeast, yeast extract, meat extract, ammonium sulphate, ammonium nitrate, ammonium chloride, ammonium phosphate and so on. As inorganic salts, there may be employed such inorganic salts as are usually required in the cultivation of microorganisms. Thus, for example, sodium chloride, potassium chloride, calcium carbonate, magnesium sulphate, potassium dihydrogen phosphate, disodium monohydrogen phosphate and so on may be employed either alone or in a suitable combination. If necessary, there may also be incorporated in the medium various heavy metal salts, vitamins and so on, as well as antifoams and surfactants (e.g. silicone oils, polyalkyleneglycol ethers, etc.). There may further be incorporated suitable amounts of organic or/and inorganic additives which assist in the growth of the microorganism and promote the production of anti-biotic P-2563.

The cultivation may be carried out in the same manner as is generally used for the production of the antibiotics. Thus, various forms of solid culture or fluid culture may be employed according to the particular requirements.

In the case of fluid culture, this may be conducted under stationary, stirring, shaking, aerated, submerged or other conditions, although aerobic submerged culture is preferred.

The cultivation is carried out under aerobic conditions. The cultivation pH range which is suitable may range from pH 4.5 to pH 9.5, and the cultivation temperature may be somewhere between 4° C and 37° C although a temperature range of 15° C to 35° C is preferred.

The production of antibiotic P-2563 reaches a maximum in 12 to 168 hours, usually in 24 to 144 hours, both for shake culture and tank culture, most of the titer occurring in the fluid part of the broth (filtered broth).

In accordance with this invention, the antibiotic P-2563 thus produced and accumulated is harvested from the culture broth. As to the harvesting procedure, there may be employed any suitable procedure which is ordinarily employed for harvesting the metabolites of microorganisms.

Since the antibiotic P-2563 is a basic substance highly soluble in water but either sparingly soluble or insoluble in the common organic solvents, procedures which are often followed in the purification of the so-called water-soluble, basic antibiotics can be employed.

Thus, for example, an adsorption-desorption cycle using a cation-exchange resin, cellulose-column chromatography, an adsorption-desorption cycle using a column of Sephadex (trade mark) LH-20 (available from Pharmaria Co., Sweden) or silica gel-column chromatography, may be employed alone or in any suitable combination.

Thus, for example, the filtered broth obtained following the removal of cells from the culture broth is adjusted to pH 7.5 and passed column-wise over Amberlite (trade mark) IRC-50($NH_4^+$-form), a cation-exchange resin available from the Rohm and Haas Company, U.S.A. The column on which the antibiotic has thus been adsorbed is first washed with water and eluted with 1N aqueous ammonia, whereupon both P-2563 emerge from the column. To separate P-2563, ion-exchange chromatography on a buffered cation-exchange resin, for example, may be expediently employed. Thus, the active fraction obtained as above is concentrated under reduced pressure and the concentrate is passed columnwise over Amberlite CG-50 ($NH_4^+$-form), a cation-exchange resin available from the Rohm and Haas Company, U.S.A., which has been buffered with 0.05N aqueous ammonia. The resin column on which the antibiotic has thus been adsorbed is developed with 0.08N aqueous ammonia at a space velocity of 1, upon which two active fractions are obtained. The first active fraction contains a compound having a propionyl group at one terminal [hereinafter referred to briefly as P-2563 (I)], and the second active fraction contains a compound being an acetyl group at one terminal [hereinafter referred to briefly as P-2563 (II)] follows.

The desired substance that is thus separated in a fairly high state of purity can be further purified by decolorisation and subsequent crystallization from an aqueous solvent, either as the free base or after conversion to a mineral acid salt. Thus, the fractions rich in P-2563 (I) and P-2563 (II) are independently pooled and concentrated under reduced pressure. The concentrate is passed columnwise over Dowex (trade mark) 1×2 (OH-form), an anion-exchange resin available from the Dow Chemical Company, U.S.A., and the adsorbed resin is eluted with water. The active eluate is neutralised with a mineral acid and concentrated under reduced pressure. The resulting syrup is dissolved in a small amount of a suitable solvent, followed by the addition of a solubility-depressing solvent such as ethanol, n-propyl alcohol, acetone, ether, ethyl acetate, cyclohexane, n-hexane or the like, whereupon P-2563 (I) and (II) is separately obtained as the hydrochloride or sulphate, for instance, depending upon the mineral acid used for the above neutralisation.

To confirm the active fractions in the above purification procedure, it is recommended that a bioassay method involving the use of a microorganism whose growth will be inhibited by P-2563 (I) or (II), e.g. *Escherichia coli* IFO-3044, should be employed in conjunction with a method comprising thin-layer chromatography with ninhydrin detection.

The following are the physical and chemical properties of antibiotic P-2563. Antibiotic P-2563 (I) free from:
(I) Appearance: white powder
(2) Elemental analysis: $C_{15}H_{31}N_3O_9$ Calcd.: C, 45.34; H, 7.81; N, 10.58. Found: (i) C, 45.05; H, 7.85; N, 10.31 (ii) C, 45.15; H, 7.89; N, 10.78.

(3) Melting point: 105 to 115° C (decomp.)

(4) Molecular formula: $C_{15}H_{31}N_3O_9$ (5) Ultraviolet absorption spectrum:

No characteristic absorption maxima but terminal absorptions at 220 to 360 m$\mu$.

(6) Optical rotation: $[\alpha]_D^{20}$ +72.3 to −73.7° (c=1.0, aqueous solution)

(7) Infrared absorption spectrum:

The absorption wave-numbers and intensities of P-2563 (I) (KBr) are as follows (cf. FIG. 11 of the accompanying drawings).

3370cm$^{-1}$(S), 2940cm$^{-1}$(M), 1650cm$^{-1}$(S), 1560cm$^{-1}$(S), 1150cm$^{-1}$(M), 1080cm$^{-1}$(S), 1030cm$^{-1}$(S), 920cm$^{-1}$(W) (S,M and W mean strong, medium and weak, respectively)

(8) Colour reaction

Molish reaction : Positive

Potassium permanganate: Positive

Ninhydrin : Positive

Ehrlich : Yellow

Sakaguchi : Negative

Fehling : Negative (9) Solubilities:

Readily soluble in water, methanol and ethanol: sparingly soluble in n-propanol, butanol and acetone; insoluble in chloroform, ethyl acetate, ether, n-hexane and petroleum ether.

(10) Stability:

Stable from pH 3 to 8; decomposes gradually with a loss of activity under strongly basic (above pH 8) and strongly acidic (below pH 3) conditions.

(11) Paper chromatography (Rf, on whatman No. 1 paper):

0.54(n-propanol-pyridine-acetic acid-water=15:10:3:12)

0.18(n-butanol-acetic acid-water=3:1:1)

0.48(ethyl acetate-n-propanol-25 % aqueous ammonia-water=1:5:1:3)

(12) Thin-layer chromatography (Tokyo Kasei K.K. Spot Film, cellulose powder):

Rf 0.51(n-propanol-pyridine-acetic acid-water=15:10:3:12)

0.22(n-butanol-acetic acid-water=3:1:1)

0.55(ethyl acetate-n-propanol-25 % ammonia-water=1:5:1:3)

Figure 12:
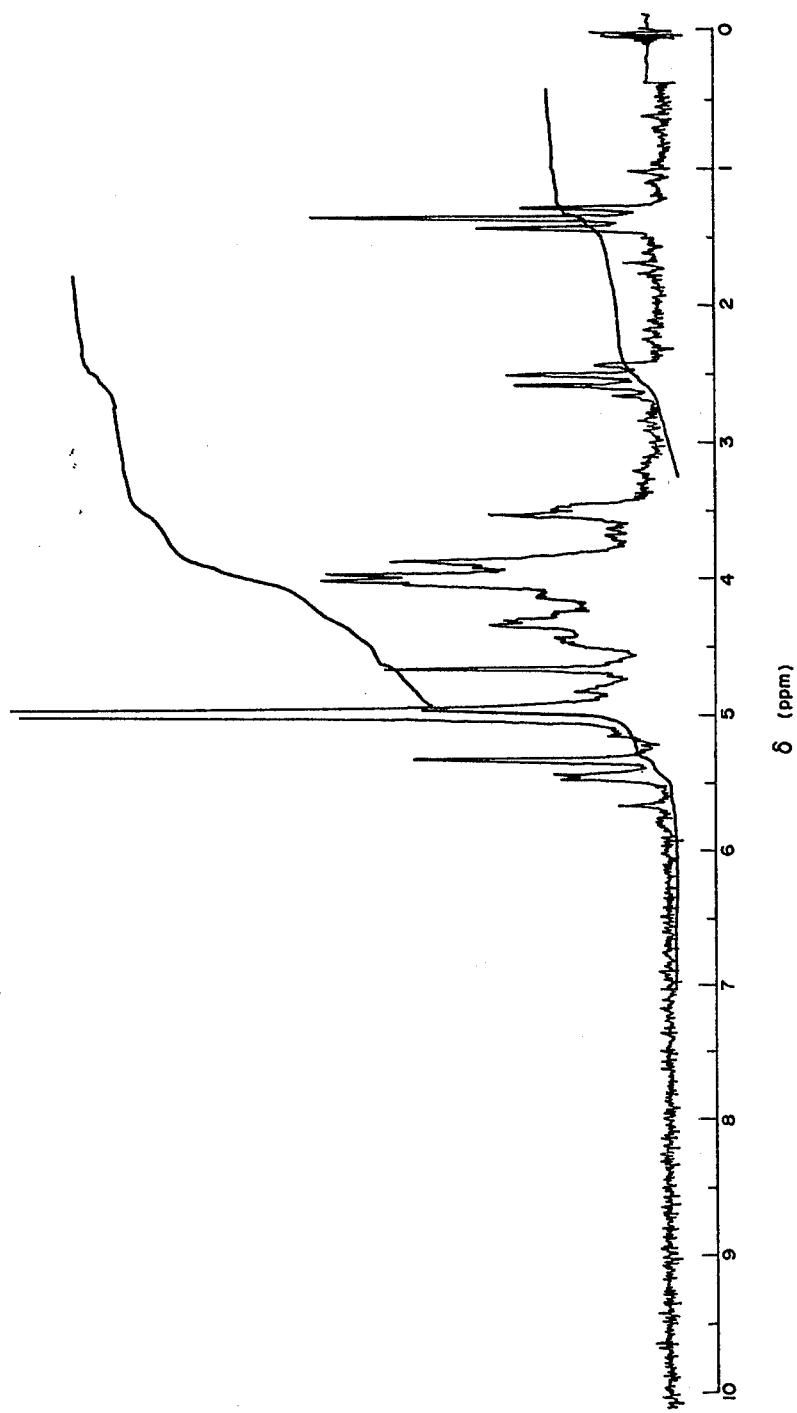

(13) Nuclear magnetic resonance spectrum:

The NMR spectrum of P-2563 (I) (100 MHz,D$_2$O) is shown in FIG. 12 of the accompanying drawings.

Antibiotic P-2563 (I) monohydrochloric acid salt:

(1) Appearance: white needles (2) Elemental analysis: $C_{15}H_{31}N_3O_9 \cdot HCl \cdot 2H_2O$ Calcd.: O, 38.34; H, 7.67; N, 8.95 Cl, 7.56; O, 37.49. Found : (i) C, 38.66; H, 7.61; N, 8.92; Cl, 7.35; O, 37.20. (ii) C, 38.49; H, 7.66; N, 8.98; Cl, 7.28; O, 37.59.

(3) Melting point: 98° to 108° C(decomp.)

(4) Molecular formula: $C_{15}H_{31}N_3O_9(HCl \cdot 2H_2O)$ (5) Ultraviolet absorption spectrum:

No characteristic absorption maxima but terminal absorptions at 220 to 360 m$\mu$.

(6) Optical rotation: $(\alpha)_D^{23}$ +60.3 to +61.3° (c=1.0, aqueous solution)

(7) Infrared absorption spectrum:

The absorption wave-numbers and intensities of P-2563 (I) hyrochloride (KBr) are as follows (cf.FIG.1 of the accompanying drawings).

3370cm$^{-1}$(S), 2910cm$^{-1}$(M), 1640cm$^{-1}$(S), 1550cm$^{-1}$(S), 1150cm$^{-1}$(M), 1085cm$^{-1}$(S), 1030cm$^{-1}$(S), 940cm$^{-1}$(W) (S, M and W mean strong, medium and weak, respectively)

(8) Colour reactions:

Molisch ration : Positive

Potassium permanganate : Positive

Ninhydrin : Positive

Ehrlich : Yellow

Saguchi : Negative

Fehling : Negative (9) Solubilities:

Readily soluble in water and methanol: sparingly soluble in ethanol, n-propanol, butanol and acetone; insoluble in chloroform, ethyl acetate, ether, n-hexane and petroleum ether.

(10) Stability:

Stable from pH 3 to 8; decomposes gradually with a loss of activity under strongly basic (above pH 8) and strongly acidic (below pH 3) conditions.

(11) Paper chromatography (on Whatman No.1 paper):

Rf 0.54(n-propanol-pyridine-acetic acid-water=15:10:3:12)

0.18(n-butanol-acetic acid-water=3:1:1)

0.48(ethyl acetate-n-propanol-25 % aqueous ammonia-water = 1:5:1:3)

(12) Thin-layer chromatography (Tokyo Kasei K.K., Japan, Spot Film, cellulose powder):

Rf 0.51(n-propanol-pyridine-acetic acid-water=15:10:3:12)

0.22(n-butanol-acetic acid-water=3:1:1)

0.55(ethyl acetate-n-propanol-25 % ammonia-water=1:5:1:3)

Figure 4:
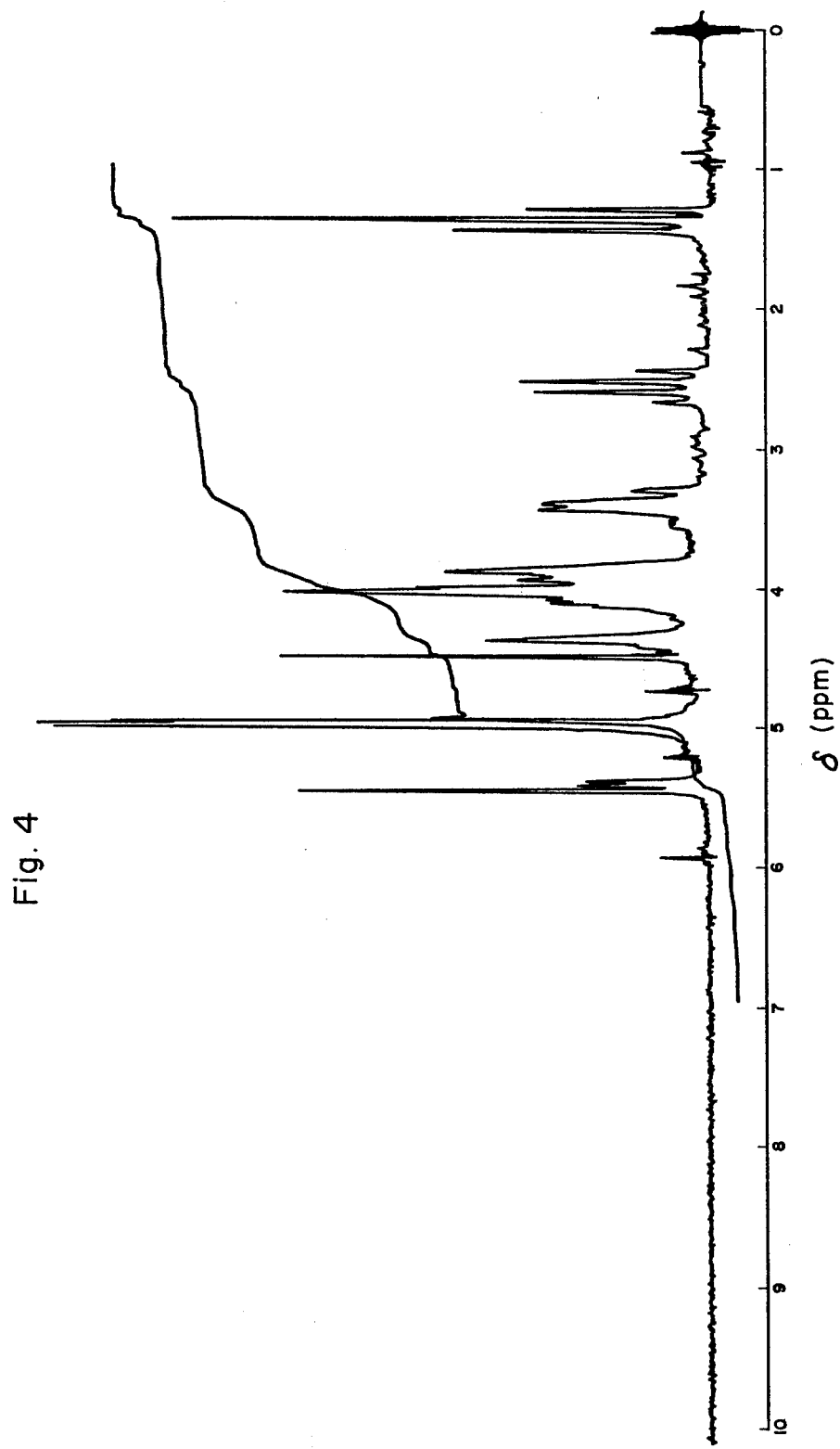

(13) Nuclear magnetic resonance spectrum:

The NMR spectrum of P-2563 (I) hydrochloride (100 MH$_z$, D$_2$O) is shown in FIG. 4 of the accompanying drawings.

The following are the physical and chemical properties of antibiotic P-2563 (II).

(1) Appearance: White crystalline powder (2) Elemental analysis: $C_{14}H_{29}N_3O_9$ Calcd. : C, 43.86; H, 7.57; N, 10.97 Found : (i) O, 43,35; H, 7.50; N, 9.92 (ii) O, 44.02; H, 7.68; N, 10.93

(3) Melting point: 148 to 152° C. (decomp.).

(4) Ultraviolet absorption spectrum:

No characteristic absorptions but terminal absorptions only between 220 m$\mu$ and 360 m$\mu$.

(5) Optical rotation: $(\alpha)_D^{23}$ +76.1 to +77.1° (c=1.0, aqueous solution)

(6) Infrared absorption spectrum:

The absorption wave-numbers and intensities of P-2563 (II) (KBr) are as follows (cf. FIG. 2 of the accompanying drawings)

3370cm$^{-1}$(S), 2950cm$^{-1}$(M), 1660cm$^{-1}$(S), 1570cm$^{-1}$(S), 1390cm$^{-1}$(S), 1320cm$^{-1}$(S), 1150cm$^{-1}$(M), 1080cm$^{-1}$(S), 1035cm$^{-1}$(S), 560cm$^{-1}$(W) (S, M and W denote strong, medium and weak, respectively)

(7) Colour reactions:

Molich : Positive

Potassium permanganate : Positive

Ninhydrin : Positive

Ehrlich : Yellow

Sakaguchi : Negative

Fehling : Negative (8) Solubilities:

Readily soluble in water and methanol; sparingly soluble in ethanol, n-propanol, butanol and acetone; insoluble in chloroform, ethyl acetate, ether, n-hexane and petroleum ether.

(9) Stability:

Stable over pH 3 to 8; decmposes gradually with a loss of activity under strongly basic (above pH 8) and strongly acidic (below pH 3) conditions.

(10) Thin-layer chromatography (Tokyo Kasei K.K., Japan, Spot Film, cellulose powder)

Rf  0.41(n-propanol-pyridine-acetic acid-water=15:10:3:12)

0.10(n-butanol-acetic acid-water=3:1:1)

0.46(ethyl acetate-n-propanol-25 % ammonia-water=1:5:1:3)

Figure 5:
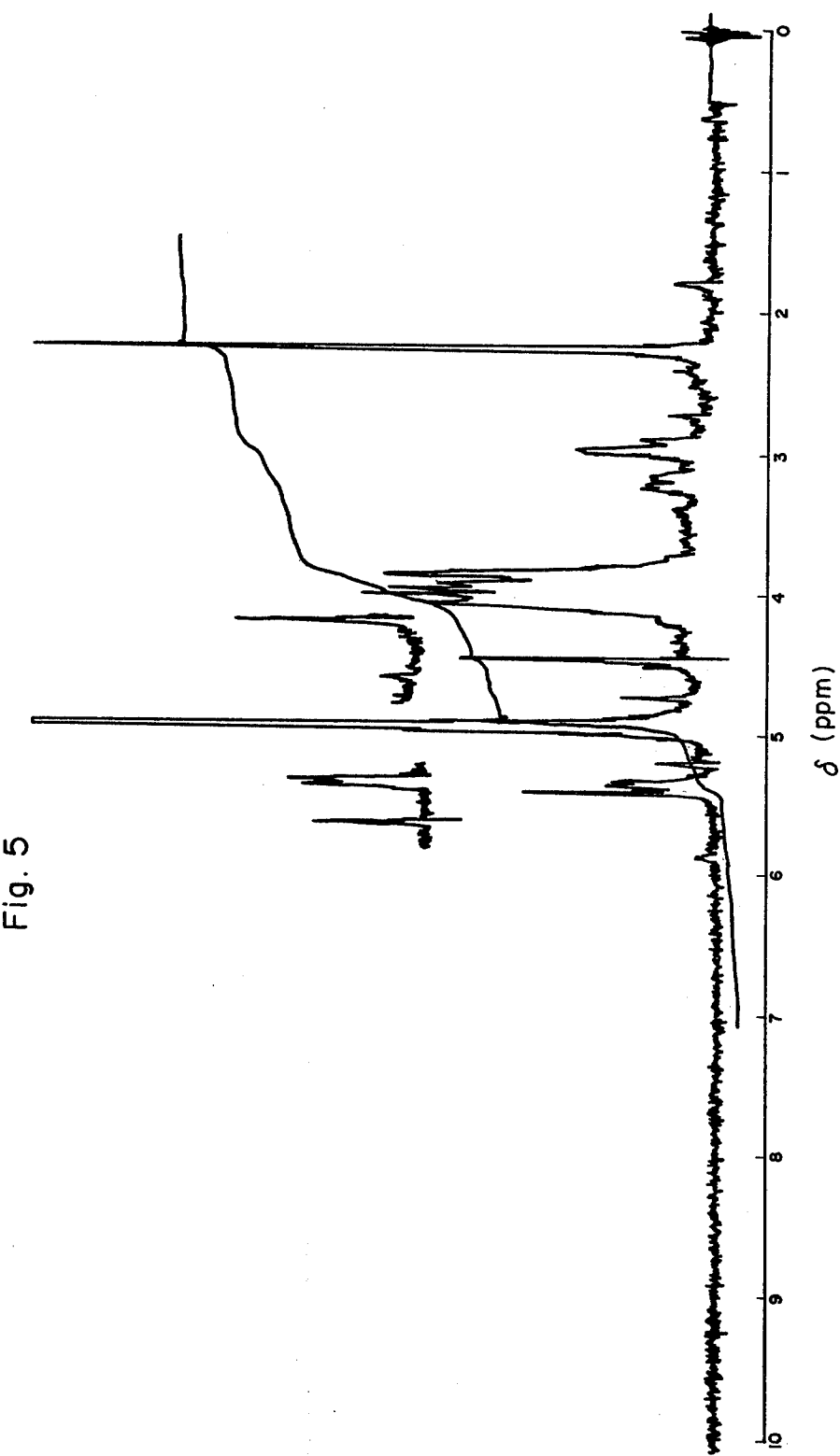

(11) Nuclear magnetic resonance spectrum:

The NMR spectrum (100 MHz, $D_2O$) of P-2563 (II) is shown in FIG. 5 of the accompanying drawings.

It should, however, be noticed that P-2563 (I) and (II) are interconvertible; that is to say, one of them may be derived from the other; and also that, as to compounds in which R is an acyl group other than acetyl and propionyl, such a compound can be obtained, for example, by the steps of protecting the free amino group of P-2563 (I) or P-2563 (II) with suitable protective groups, hydrolysing the acetylamino or propionylamino moiety to a free amino group, subjecting this amino group to an acylation reaction and thereby converting the same amino group to the desired acylamino group and finally removing the protective group. Thus, for example, if antibiotic P-2563 (I) is dissolved in aqueous ethanol to prepare a dilute alkaline solution and is then reacted with p-methoxy-benzaldehyde, there is obtained N-p-methoxybenzylidene-P-2563 (I). If the last-mentioned compound is dissolved in tetrahydrofuran-methanol (3:2) and reduced with $NaBH_4$, there is obtained N-p-methoxybenzyl-P-2563 (I). If this lastmentioned compound is hydrolysed by heating in 1N NaOH, the propionyl group is split off, leaving N-p-methoxybenzyl-$f_3$. This last compound is dissolved in ethylene glycol dimethylether containing 50% of water, and reacted with an acetylaminating agent such as acetyl chloride, whereby N-p-methoxybenzyl-P-2563 (II) is obtained. The reaction mixture is concentrated under reduced pressure, dissolved in dioxane containing 50% of water and reduced with molecular hydrogen in the presence of a 10% palladium-on-charcoal catalyst. In this manner, antibiotic P-2563 (II) can be easily obtained.

In this connection, by causing propionyl chloride to act upon the aforementioned N-p-methoxybenzyl-$f_3$, P-2563 (I) can be resynthesized. Therefore, by reacting said N-p-methoxybenzyl-$f_3$ with various acid chlorides, e.g. butyryl chloride, isobutyryl chloride, valeryl chloride, isovaleryl chloride, etc., there can be produced the corresponding acyl derivatives, e.g. butyryl, isobutyryl, valeryl, isovaleryl and other compounds.

When decomposed with an alkali, P-2563 (I) yields substance $f_3$ a ninhydrin positive substance (hereinafter referred to briefly as P-2563 (III)) and propionic acid.

Antibiotic P-2563 (III) has the following physico-chemical properties.

(1) Elemental analysis: $C_{12}H_{27}N_3O_8$

Calcd. C, 42.23; H, 7.92; N, 12.32 Found (i) C, 42.08; H, 7.90; N, 12.22 (ii) C, 42.51; H, 7.95; N, 12.01

(2) Appearance: white powder (3) Melting point: 110 to 117° C (decomp.)

(4) Ultraviolet absorption spectrum:

No characteristic absorption maxima but terminal absorptions at 220° to 360 mµ.

(5) Optical rotation: $(\alpha)_D^{20}$ +81.4 to +83.4°(c=1, $H_2O$)

Figure 9:
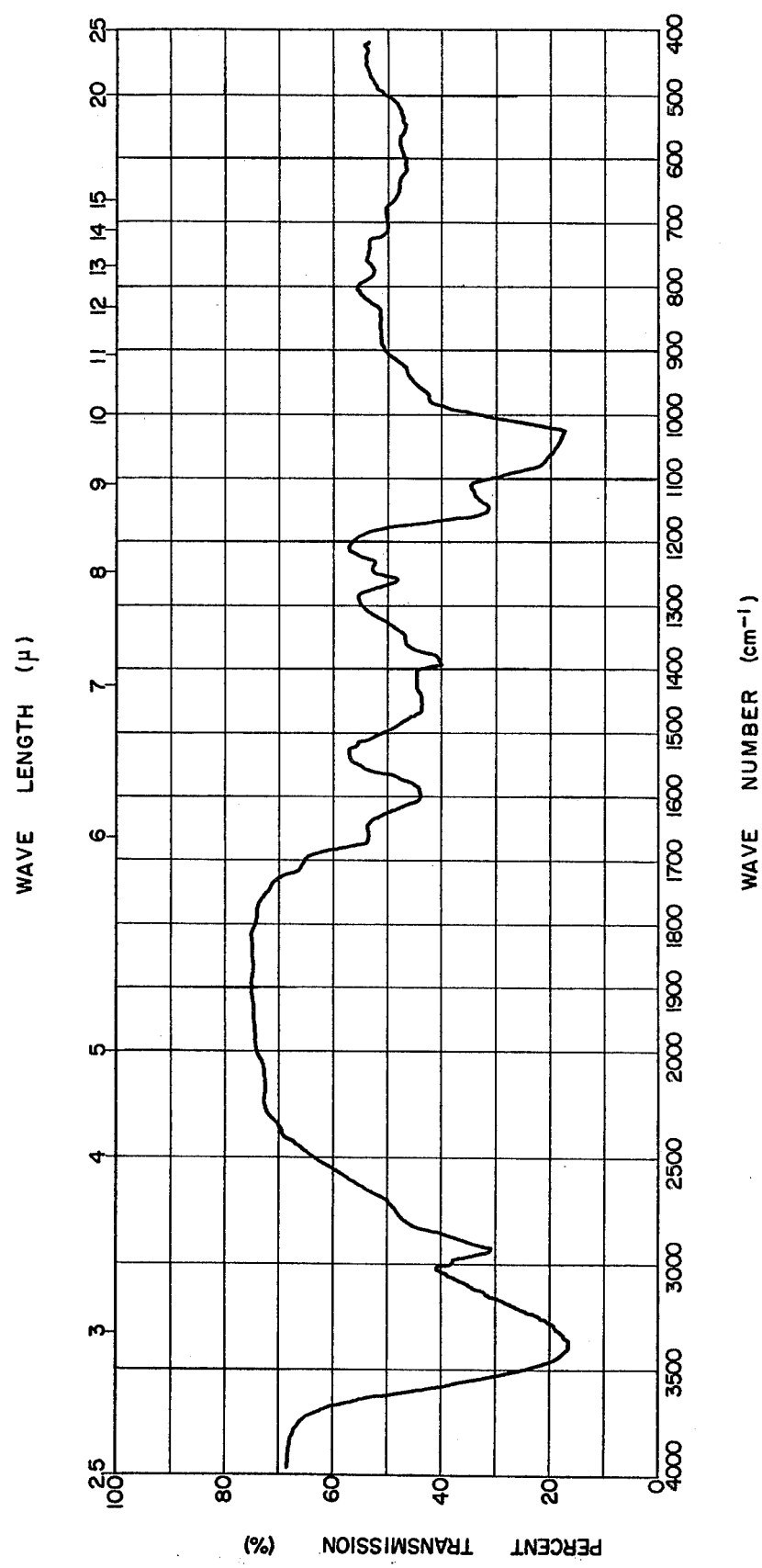

(6) Infrared absorption spectrum: (FIG. 9)

The absorption wave-numbers and intensities of "f3" (KBr) are as follows.

3,370$cm^{-1}$(S), 2,940$cm^{-1}$(M), 1,600$cm^{-1}$(M), 1,390$cm^{-1}$ (M), 1,150$cm^{-1}$(S), 1,030–1,080$cm^{-1}$(S). (S, M, and W mean strong, medium and weak, respectively)

(7) Colour reactions:

Molich reaction : positive

Potassium permanganate : positive

Ninhydrin : positive

Ehrlich : Yellow

Sakaguchi : Negative

Fehling : Negative (8) Solubilities:

Readily soluble in water and methanol; sparingly soluble in ethanol, n-propanol, butanol and acetone; insoluble in chloroform, ethylacetate, ether, n-hexane and petroleum ether.

(9) Stability

Stable from pH 3 to pH 13: decomposes gradually under strongly acidic (below pH 3) and strongly basic (above pH 13) conditions.

(10) Thin-layer chromatography (Silica gel precoated TLC plates available from E. Merck, West Germany)

Rf  0.05  (n-propanol-pyridine-acetic acid-water=15:10:3:12)

0.02(n-butanol-acetic acid-water=3:1:1)

0.13(ethylacetate-n-propanol-25% ammonia-water=1:5:1:3)

Figure 10:
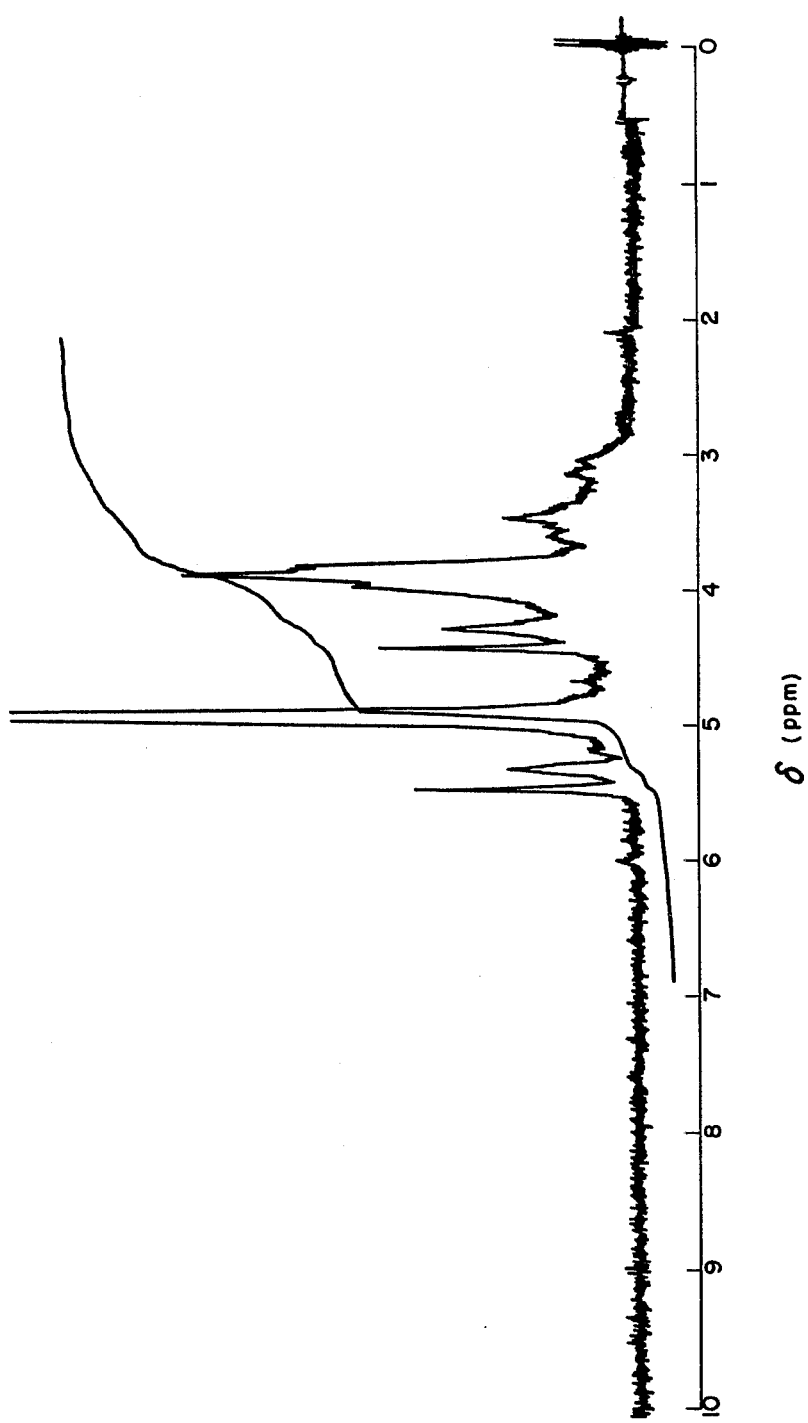

(11) Nuclear magnetic resonance spectrum:

The NMR spectrum of "$f_3$" (100 MHz, in $D_2O$) is shown in FIG. 10 of the accompanying drawings.

The antibiotic P-2563 (III) (substance $f_3$) can be prepared by decmposing P-2563 (I) or P-2563 (II) with akaline reagents such as an aqueous solution of 0.1–1.0 normal of sodium hydroxide or barium hydroxide or a suspension of strong anion exchange resin such as Amberlite IRA-400 ($OH^-$) (Rohm and Haas Co., U.S.A.), Dowex 1×2 ($OH^-$) (Dow Chemical Co., U.S.A.), or acidic reagents such as an aqueous solution of 0.1–1.0 normal of hydrochloric acid, of sulfuric acid, or a suspension of a strong cation exchange resin Amberlite IR-120 ($H^+$) (Rohm and Haas Co., U.S.A.), Dowex 50×8 ($H^+$) (Dow Chemical Co., U.S.A.) at 30° C–100°C.

On methanolysis with HCl-saturated methanol, the substance $f_3$ yields two ninhydrin-positive substances (hereinafter referred to as 'substance $f_6$' and substance $f_2$, respectively).

The 'substance $f_6$' has the following physical and chemical properties.

(1) Elemental analysis (found) (i) C, 42.96; H, 7.82; N, 7.01 (ii) C, 43.14; H, 7.81; N, 7.08

(2) Mass spectrum:

m/e=193($M^+$), 162($M^+$-$OCH_3$)

The above properties, (1) and (2) suggest that 'substance $f_6$' is a methylglucoside having a molecular formula of $C_7H_{15}NO_5$. When 'substance $f_6$' is acetylated with acetic anhydride-pyridine and subjected to thin-layer chromatography on silica gel with ethyl acetate as a developer solvent, there are obtained two substances giving positive Molisch's reactions, namely a first substance at Rf=0.4(hereinafter referred to as 'substance Rf 0.4($f_{6a}$)') and a second substance at Rf=0.3(hereinafter referred to 'substance Rf 0.3 ($f_{6b}$)').

The 'substance Rf 0.4($f_{6a}$)' has the following physical and chemical properties.

(1) Appearance: White needles (2) Elemental analysis: $C_{15}H_{23l NO9}$
Calcd. : C, 49.86; H, 6.37; N, 3.88 Found : C, 49.88; H, 6.34; N, 3.85

(3) Melting point: 138° to 140° C.

(4) Mass spectrum: m/e=361(M$^+$), 330(M$^+$—OCH$_3$)

(5) Optical rotation: $(α)_D^{23}$ +156° (c=1.0, in chloroform)

(6) Infrared absorption spectrum: $_{max}^{KBr}$ 3350 cm$^{-1}$ (NH),
1740cm$^{-1}$ (acetate C=O), 1670cm$^{-1}$(amide C=O), 1540cm$^{-1}$ (amide II)

From the above physical and chemical properties and its nuclear magnetic resonance spectrum, 'substance Rf 0.4 ($f_{6a}$)' was elucidated to be methyl-4acetamido-2,3,6-tri-0-acetyl-4-deoxy-α-D-glucopyranoside which is described in J. Org. Chem. 30, 2312-2317(1965) and the same Journal 30(4), 1085-1088(1965). As for 'substance Rf 0.3($f_{6b}$)', it is assumed from its elemental analysis, melting point, optical rotation, mass spectrum, infrared absorption spectrum and nuclear magnetic resonance spectrum that this substance is methyl-4-acetamido-2,3,6-tri-0-acetyl-4-deoxy-β-D-glucopyranoside which is an anomer of the aforementioned 'substance Rf 0.4($f_{6a}$)'.

The molecular formula of 'substance P-2563 (I) $f_2$' was found to be $C_6H_{16}N_2O_4$, in the light of:- a. the fact that 'substance P-2563(I)$f_2$' obtained by the procedure described in Example 4 given hereinafter has a melting point of 108 to 110° C, an optical rotation value $[α]_D^{25}$ of −1.4 to −2.4° (c=1.0, in H$_2$O) and an elemental analysis (found) of (i) C, 39.08; H, 8.96; N, 15.14
(ii) C, 38.79; H, 8.97, N, 15.50 b. based on its infrared absorption spectrum (FIG. 3 of the accompanying drawings) and nuclear magnetic resonance spectrum (FIG. 6); and c. based on the fact that, on acetylation of 'substance P-2563(I) $f_2$' with acetic anhydride-pyridine, there is obtained the corresponding hexaacetate which gives an elemental analysis (found) of (i) C, 49.64; H, 6.47; N, 6.49
(ii) C, 49.22; H, 6.37; N, 6.42 with its mass spectrum giving an m/e value of 433 (M$^+$ +1), and, therefore, this hexaacetate has a molecular formula of $C_{18}H_{28}N_2O_4$.

Analysis of the nuclear magnetic resonance spectra of 'substance P-2563 (I) $f_2$', hexaacetate (solvent CDCl$_3$- FIG. 7 of the accompanying drawings; solvent CDCl$_3$ + D$_2$O -FIG. 8 of the accompanying drawings) shows that 'substance P-2563 (I)$f_2$' is 3,6-diamino-3,6-dideoxy-hexitol which is a new compound of the following structural formula [2]:

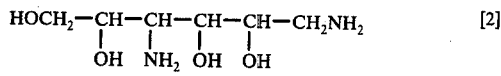

Thus, 3,6-diamino-3,6-dideoxy-hexitol which is a constituent moiety of the present antibiotic is of great value as a starting material from which various antibiotics and other pharmaceutically active derivatives can be derived by chemical modifications.

The above results suggested that the antibiotic P-2563 (I) consists of propionic acid, 4-amino-4-deoxy-D-glucose and 3,6-diamino-3,6-dideoxy-hexitol, a new amino alcohol, and has the chemical structure of the general formula (I) wherein R is propionyl.

In the light of the fact that the antibiotic P-2563 (II), on decomposition with an alkali, yields acetic acid and a ninhydrin-positive substance $f_3$. The above results suggests that the antibiotic P-2563 (II) has the chemical structure of the general formula (I) wherein R is acetyl.

The antibiotic P-2563 forms salts with acids such as hydrochloric acid, sulfuric acid, hydrobromic acid, acetic acid, oxalic acid and so on. The present invention covers these salts. The physico-chemical properties of hydrochloric acid and sulfuric acid salts of antibiotic P-2563 (I) are shown below:

Di-hydrochloric acid salt of antibiotic P-2563(I)

(1) Appearance: white powder (2) Elemental analysis: $C_{15}H_{31}N_3O_9·2HCl$ Calcd.: C, 38.30; H, 7.02; N, 8.94; Cl, 15.11 Found : C, 38.80; H, 7.32; N, 8.32; Cl, 14.85

(3) Melting point: 170° to 175° C(Decomp.)

The physico-chemical properties of monohydrochloric acid salt of antibiotic P-2563 (I) have been previously shown. Sulfuric acid salt of antibiotic P-2563(I)

(1) Appearance: white powder (2) Elemental analysis: $C_{15}H_{31}N_3O_9·H_2SO_4$ $_{Calcd.: C,}$ 36.36; H, 6.67; N, 8.48; S, 6.46 Found : C, 35.95; H, 6.81; N, 7.99; S, 6.48

(3) Melting point: 200 to 210° C(decomp.)

The antibiotic of this invention will hereinafter be compared with known antibiotics. As described hereinbefore, antibiotics P-2563 (I), (II) and (III) have the molecular formulae $C_{15}H_{31}N_3O_9$, $C_{14}H_{29}N_3O_9$, and $C_{12}H_{27}N_3O_8$ respectively, and each includes an 4-amino-4-deoxy-D-glucose as its constituent amino-sugar moiety and a 3,6-diamino-3,6-dideoxy-hexitol moiety which is a new aminoalcohol. They are water-soluble basic anti-biotics of low toxicity, showing a broad antimicrobial spectrum, especially against gram-positive and gram-neg ative bacteria. Among known antibiotics which are water-soluble and basic and, at the same time, have broad antimicrobial spectra, there may be mentioned gentamicin, ribostamycin, kanamycin A, B and C tobramicin, hybrimycin A$_3$, kasugamycin, hydromycin, LL-AC 541, LL-AB 664, and so on. However, the antibiotics P-2563 (I), (II) and (III) are clearly distinct from the known antibiotics: e.g. from kasugamycin, in antimicrobial spectra; from hygromycin, in terms of toxicity; and from other known antibiotics in antimicrobial spectrum and antibiotic potency. Comparison with water-soluble, basic aminoglycoside antibiotics which, in properties, are considered to be somewhat similar to antibiotics P-2563 (I), (II) and (III), e.g. mojirimycin, trehalosamine, actinospectacin, fortimycin B, neomycin A (neamine), paromamine, gentamine, etc., shows that the present antibiotics are evidently distinct from such known antibiotics: for example, from nojirimycin, trehalosamine, actinospectacin, neomycin A (neamine), paromamine and gentamine in infrared absorption spectrum, and from fortimycin B in nitrogen content. Furthermore, judged from the nuclear magnetic resonance and mass spectra, there is no hitherto-known antibiotic that has the same chemical structure as the present antibiotic.

Thus, both the antibiotics P-2563 (I), (II) and (III) are novel antibiotics. The antibiotic activity of the present antibiotic will hereinafter be described.

The antimicrobial spectra of antibiotics P-2563 (I) and P-2563 (II) are shown in Table 2 below.

In the table, procedures I to III mean the following:
Procedure I : Cultivated on heart infusion agar medium (Difco) at 37° C for 24 hours.
Procedure II : Cultivated on heart infusion agar medium with 1 % added glycerin at 37° C for 48 hours.
Procedure III : Cultivated on glucose bouillon agar medium at 28° C for 96 hours.

It is clear from this table that the antibiotics P-2563 (I) and P-2563 (II) are inhibitory to gram-positive and gram-negative bacteria and particularly to bacteria of the genus *Pseudomonas*.

Table 2
(Antimicrobial spectra)

| No. | Assay organism | Procedure | Minimal inhibitory concentration (mcg/ml). | |
|---|---|---|---|---|
| | | | F-2563 (I) | P-2563 (II) |
| 1 | Bacillus subtilis | I | 30 | 70 |
| 2 | Staphylococcus aureus | I | 50 | 200 |
| 3 | Escherichia coli | I | 30 | 50 |
| 4 | Klebsiella pneumoniae | I | 12.5 | 50 |
| 5 | Pseudomonas aeruginosa | I | 50 | 300 |
| 6 | Proteus vulgaris | I | 30 | 100 |
| 7 | Proteus mirabilis | I | 200 | 200 |
| 8 | Mycobacterium species | II | 200 | 200 |
| 9 | Cryptococcus neoformans | III | >500 | >500 |
| 10 | Candida albicans | III | >500 | >500 |
| 11 | Aspergillus fumigatus | III | >500 | >500 |
| 12 | Microsporum gypseum | III | >500 | >500 |
| 13 | Trichophyton mentagrophytes | III | >500 | >500 |

The antibiotics P-2563 (I) and P-2563 (II) are both extremely low in toxicity, their $LD_{50}$ in mice (intravenous) being >400 mg/kg.

It will be seen from the foregoing description that the present antibiotic P-2563 is of value as a drug, for example, as an oral or external drug for the treatment antibiotic can be used as a cream or ointment containing 0.01 to 0.1 percent thereof in established formulations for local administration for men and animals. The antibiotic can also be used for disinfecting apparatuses, instruments and equipment in a 0.01 to 1.0 % aqueous solution.

The antibiotic P-2563 is a class of aminocyclitol antibiotic having a new skeletal structure and is of great value as a starting compound from which various derivatives can be synthesized by chemical modification.

For further detailed explanation to the invention, the following examples and reference examples are given, wherein the term "part(s)" means "weight(s)", unless otherwise noted and the relationship between "part(s)" and "part(s) by volume" corresponds to that between "gram(s)" and "milliliter(s)", and all percentages are weight/volume percentages.

EXAMPLE 1

The growth of *Pseudomonoas fluorescens* P-2563 (ATCC-31125) on a nutrient agar slant medium was picked and used to inoculate 500 parts by volume of a medium of the following composition in a Sakaguchi flask of 2,000 parts by volume capacity, previously sterilised with steam at 120° C, for 20 minutes. The medium contained 2 % of glucose, 0.5 % of yeast extract, 0.5 % of corn steep liquor, 0.5 % of peptone and 0.5 % of calcium carbonate. The inoculated medium was incubated on a reciprocating shaker at 28° C, for 48 hours. The culture thus prepared was used as a seed.

A fermentation tank of stainless steel with a capacity of 50,000 parts by volume was charged with 35,000 parts by volume of a medium composed of 4 % of glucose, 0.5 % of yeast extract, 0.5 % of corn steep liquor, 0.5 % of soybean flour, 0.5 % of cotton seed flour, 0.5 % of sodium chloride, 0.1 % of magnesium sulphate and 0.5 % of calcium carbonate, and the contents were adjusted to pH 6.8 with 30 % sodium hydroxide.

The tank was sterilised by steaming at 120° C, for 20 minutes, after which it was inoculated with the above seed.

The cultivation was carried out at a temperature of 28° C, under sparging at 14 l/min. and at 200 r.p.m. The activity against *Escherichia coli* IFO-3044 of the culture broth reached a peak in 72 hours. The resulting broth (28,000 parts by volume) was thoroughly mixed with 1,000 parts of Hyflo-standard-supercel (available from Johns Manville Products Co., U.S.A.).

The mixture was filtered through a pressure filter to obtain 27,000 parts by volume of filtered broth. This filtered broth was passed column-wise over 3,000 parts by volume of Amberlite IRC-50($NH_4^+$-form, available from the Rohm and Haas Company, U.S.A.). The column was first washed with 8,000 parts by volume of water and then eluted with 1N aqueous ammonia, the eluate being collected in 1,000 parts by volume fractions. The fractions active against *Escherichia coli* IFO-3044 (No. 3 through No. 6) were pooled and concentrated to recover 400 parts by volume of a concentrate. This concentrate was further passed column-wise over 600 parts by volume of Amberlite CG-50($NH_4^+$-form, Type I, available from Rohm and Haas Company, U.S.A.), whereby the antibiotic was adsorbed on the resin. The column was first washed with 3,000 parts by volume of water and then eluted with 0.08N aqueous ammonia, the eluate being collected in 200 parts by volume fractions. Each fraction was spotted on a silica gel spot film (available from Tokyo Kasei K.K., Japan) and developed with n-propanol-pyridine-acetic acid-water (15:10:3:12), ninhydrin being used as a colour reagent.

The fractions No. 10 to No. 21 containing the component corresponding to P-2563 (I) and the fractions No. 22 to No. 30 containing the component corresponding to P-2563 (II) were respectively pooled.

The combined fractions containing P-2563 (I) were concentrated and, after the ammonia had been substantially removed, the residue was dissolved in substantially 50 parts by volume of water. The solution was run onto a column containing 100 parts by volume of Dowex 1×2 ($OH^-$-form, available from Dow Chemical Company, U.S.A.), and elution was carried out with 500 parts by volume of water. The effluent and eluate were combined, neutralized to pH 6.5 with hydrochloric acid and concentrated under reduced pressure. The resulting syrup (substantially 20 parts by volume) was dissolved in about twice its volume of methanol and, following the addition of 100 parts by volume of ethanol, n-propanol was further added. The addition of n-propanol was terminated when white turbidity had occurred, and the mixture was held in a refrigerator, whereupon P-2563 (I) monohydrochloride separated. The mixture was kept in the refrigerator for 1 to 2 days until the crystallization was complete and, then, the crystals were collected by filtration. The wet crystals were dried in vacuo and at 50° C, for 16 hours, whereby 2.5 parts crystals of P-2563 (I) monohydrochloride·$2H_2O$ were obtained.

On the other hand, the fractions containing P-2563 (II) were pooled and concentrated under reduced pressure. After the ammonia had been sufficiently removed, the concentrate was dissolved in substantially 50 parts by volume of water. The solution was passed columnwise over 100 parts by volume of Dowex 1×20 ($OH^-$-form, available from Dow Chemical Co., U.S.A.), and elution was carried out with 500 parts by volume of water. The effluent and eluate were combined and concentrated under reduced pressure. To about 20 parts by volume of the resulting syrup were added about 100 parts by volume of acetone, whereby P-2563 (II) separated out. The powdery precipitate was recovered by filtration and dried in vacuo and at 70° C, for 24 hours. The above procedure provided 2.1 parts of P-2563 (II) as a white powder.

EXAMPLE 2

A fermentation tank of stainless steel with a capacity of 200,000 parts by volume was charged with 100,000 parts by volume of a medium composed of 8 % soybean oil, 0.5 % of corn steep liquor, 0.5 % of yeast extract, 0.5 % of cotton seed flour, 0.3 % of ammonium nitrate, 0.025 % of monopotassium dihydrogen phosphate and 0.06 % of dipotassium monohydrogen phosphate. The medium was adjusted to pH 6.8 with 30 % sodium hydroxide and sterilized by steaming at 120° C, for 20 minutes. The sterilized medium was inoculated with 1,000 parts by volume of the same seed culture as that used in Example 1.

The cultivation was carried out at a temperature of 28° C, under sparging at the rate of 30 liters/min. and at 150 r.p.m. The activity of the culture broth against *Escherichia coli* IFO-3044 reached a peak in 72 hours. By the same procedure as that described in Example 1, the resulting culture broth was fractionated into P-2563 (I) and P-2563 (II), each of which was then purified.

The above procedure yielded 9.0 parts of P-2563 (I) monohydrochloride·$2H_2O$ crystals, and 23.0 parts of P-2563 (II) as a white powder.

EXAMPLE 3

To 28,500 parts by volume of a culture broth, prepared under the same conditions as those described in Example 1, there were added 3,000 parts by volume of Amberlite IRC-50 ($NH_4^+$-form, available from Rohm and Haas Company, U.S.A.), and the mixture was stirred gently for 3 hours, whereby P-2563 (I) and (II) were adsorbed.

The stirring was then ended and the mixture was allowed to stand, thereby causing the ion-exchange resin to settle. The resin was separated from the supernatant liquor by decantation. To this ion-exchange resin were added about 30,000 parts by volume of water and, after a short time of stirring, the mixture was allowed to stand. The resin was separated from the supernatant liquor. The resin which had thus adsorbed P-2563 (I) and (II) was packed into a column and elution was carried out with 1N aqueous ammonia to obtain 4,000 parts by volume of fractions active against *Escherichia coli* IFO-3044. The fractions were pooled and concentrated under reduced pressure to 500 parts by volume. By the same procedure as that described in Example 1, this concentrate was passed columnwise over 600 parts by volume of Amberlite CG-50($NH_4^+$-form, Type I, available from Rohm and Haas Company, U.S.A.) whereby the antibiotic was adsorbed on the resin. Elution was carried out with 0.08N aqueous ammonia to recover 2,000 parts by volume of P-2563 (I) fractions and 3,000 parts by volume of P-2563 (II) fractions. The P-2563 (I) fractions were pooled and concentrated under reduced pressure and, after the ammonia had been sufficiently removed, the concentrate was dissolved in 50 parts by volume of water. The solution was decolorised by passage through a column containing 100 parts by volume of Dowex 1×2 ($OH^-$-form, available from The Dow Chemical Co., U.S.A.), followed by elution with water. The effluent and eluate were combined, neutralized to pH 6.5 with sulfuric acid and concentrated under reduced pressure.

To 20 parts by volume of the resulting syrup were added 20 parts by volume of methanol, followed by the addition of 500 parts by volume of acetone. The procedure yielded 3.0 parts of P-2563 (I) sulphate as a crystalline powder.

On the other hand, 3,000 parts by volume of P-2563 (II) fractions were pooled and concentrated under reduced pressure. After the ammonia had been sufficiently removed, the concentrate was dissolved in 50 parts by volume of water. The solution was decolorised by passage through a column of 100 parts by volume of Dowex 1×2 ($OH^-$-form, available from The Dow Chemical Co., U.S.A.), followed by elution with water. The effluent and eluate were combined, adjusted to pH 6.5 with sulfuric acid and concentrated under reduced pressure. To about 25 parts by volume of the residual syrup were added 250 parts by volume of acetone, whereupon 3.6 parts of P-2563(II) were obtained as a powdery product.

EXAMPLE 4

In 50 parts by volume of an aqueous 0.5N solution of sodium hydroxide were dissolved 5.0 parts of P-2563 (I), and hydrolysis was carried out by boiling the solution for 1 hour. The reaction mixture was diluted with 500 parts by volume of water and the diluted solution was passed column-wise over 1,000 parts by volume of Amberlite IRC-50 ($NH_4^+$-form, available from the Rohm and Haas Company, U.S.A.). The column was first washed with 3,000 parts by volume of water and then eluted with 1N aqueous ammonia, the eluate being collected in 200 parts by volume of fractions.

To detect the active fractions each fraction was spotted on a silica gel spot film (available from E. Merck, West Germany) developed with n-propanol-pyridine-acetic acid-water (15:10:3:12), ninhydrin being used as a colour reagent.

The fractions No. 10 to No. 20 containing the component corresponding to f3 [P-2563 (III)] were pooled.

The combined fractions containing f3 [P-2563 (III)] were concentrated and, after the ammonia had been substantially removed, the residue was dissolved in 50 parts by volume of water. The solution was run onto a column containing 100 parts by volume of Dowex 1×2 (CH⁻-form, available from Dow Chemical Company, U.S.A.), and elution was carried out with 500 parts by volume of water. The effluent and eluate were combined and concentrated under reduced pressure. To the resulting syrup (substantially 20 parts by volume) was added 100 parts by volume of acetone, whereupon f3 [P-2563 (III)] is precipitated. The precipitate was collected by filtration. The wet precipitate was dried in vacuo and at 40° C for 16 hours, whereby 3.0 parts of powder of f3 [P-2563 (III)] was obtained.

REFERENCE EXAMPLE 1

In 500 parts by volume of a 6.8N methanolic solution of hydrogen chloride were dissolved 5.0 parts of P-2563 (I) hydrochloride, and methanolysis was carried out by boiling the solution for 2 hours. The reaction mixture was concentrated under reduced pressure to substantial dryness. The concentrate was dissolved in substantially 50 parts by volume of water and the solution was passed through a column of 150 parts by volume of Amberlite IR-45 (OH⁻-form, available from Rohm and Haas Company, U.S.A.) to remove the hydrochloric acid. The effluent was passed columnwise over 300 parts by volume of Amberlite CG-50 (NH₄⁺-form, available from Rohm and Haas Company, U.S.A.). After the column was washed with 500 parts by volume of water, elution was carried out by the gradient method using 750 parts by volume of water and 750 parts by volume of 1.5N NH₄OH. The eluate was collected in 15 parts by volume fractions, the 'substance $f_2$' emerging in fractions No. 70 to No. 90.

To detect the 'substance $f_2$', a thin-layer chromatoplate (silica gel, Merck, U.S.A.) was used as a support and n-propanol-pyridine-acetic acid-water (15:10:3:12) as a developer solvent system. After drying in air, the chromatogram was treated with ninhydrin, whereupon a violet spot appeared at an Rf value of substantially 0.2. The fractions containing 'substance $f_2$' were pooled and concentrated under reduced pressure to yield substantially 20 parts by volume of a syrup. This syrup was decolorised by passage through a column containing 10 parts by volume of Dowex 1×2 (OH⁻-form, available from Dow Chemical Co., U.S.A.), and concentrated under reduced pressure to substantial dryness. As the residue was allowed to stand in a refrigerator, white needles separated out. The crystals were recovered by filtration and dried under reduced pressure, and at 50° C for 16 hours. The procedure yielded 1.1 part of 'substance P-2563 (I) f₂'.

Melting point: 108°-110° C; optical rotation $[\alpha]_D^{23}$-1.4 to -2.4°(c=1.0, in water).

REFERENCE EXAMPLE 2

By a procedure similar to that described in Reference Example 1, 5.0 parts of P-2563 (II) were subjected to methanolysis, purified and crystallized, whereby 1.2 part of 'substance P-2563 (II)' were obtained. Melting point: 108°-110° C; optical rotation $[\alpha]_D^{23}$-1.85° (c=1.0, in water).

Mixture-melting with 'substance P-2563 (I) $f_2$' shows no depression in melting point.

Figure 2:
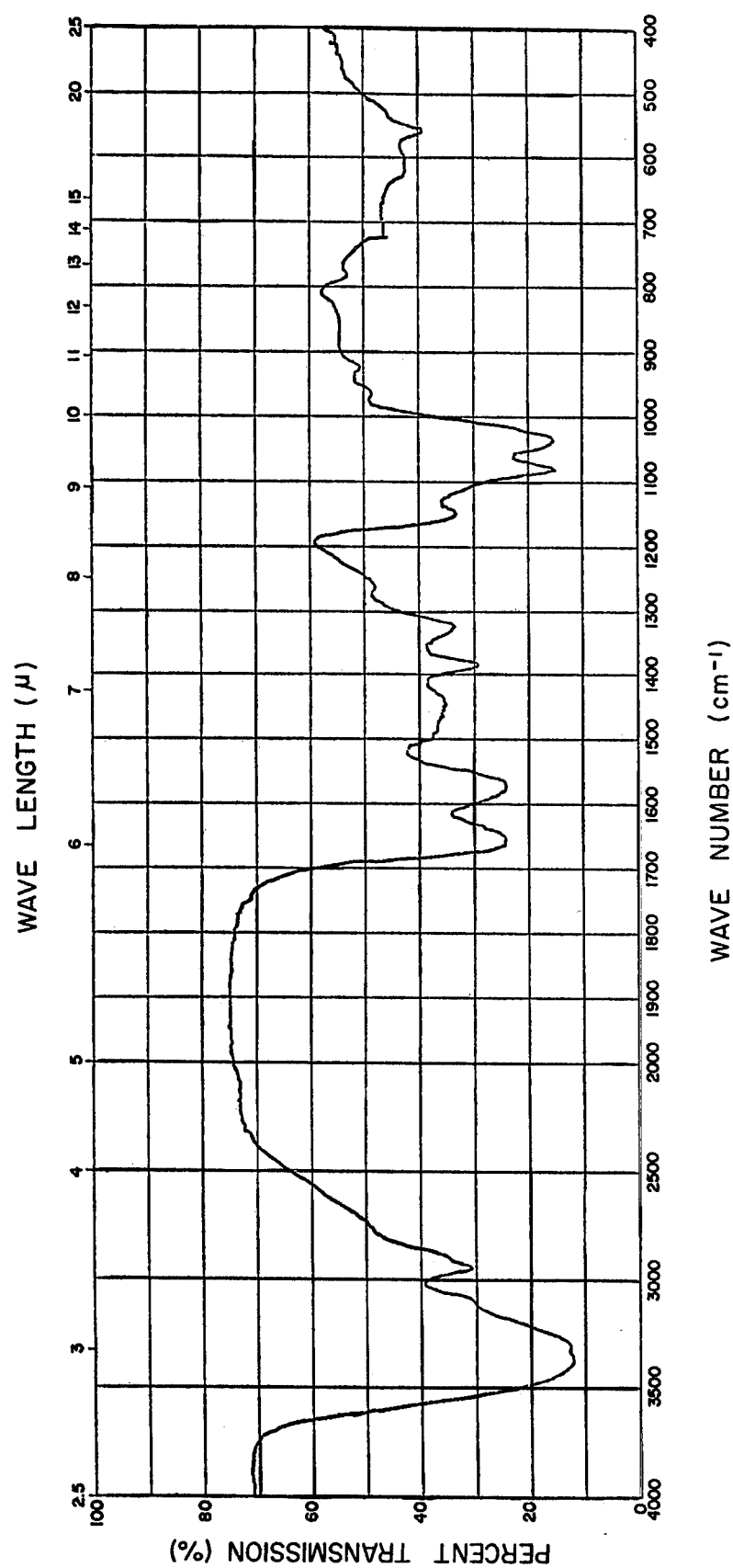
Figure 3:
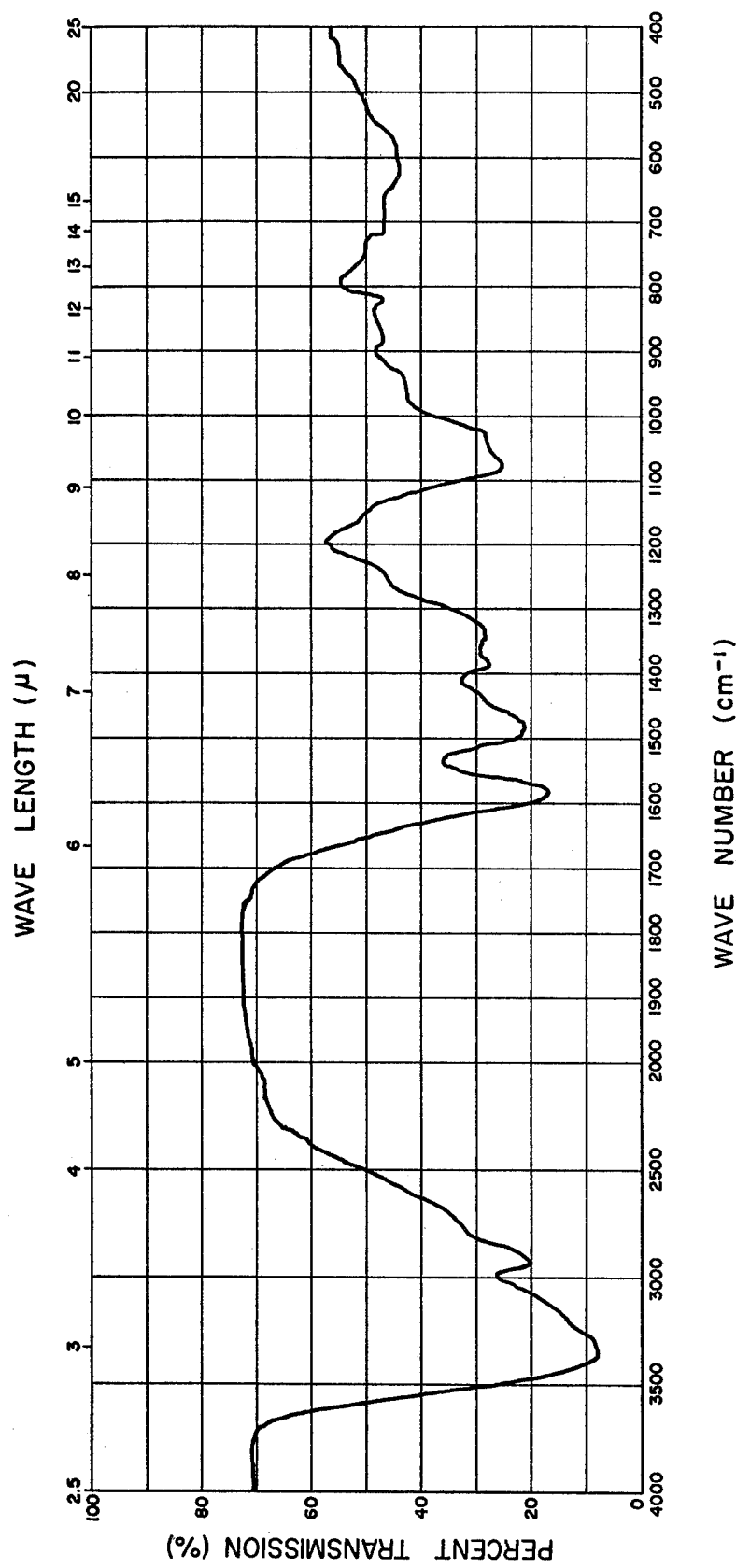
Figure 6:
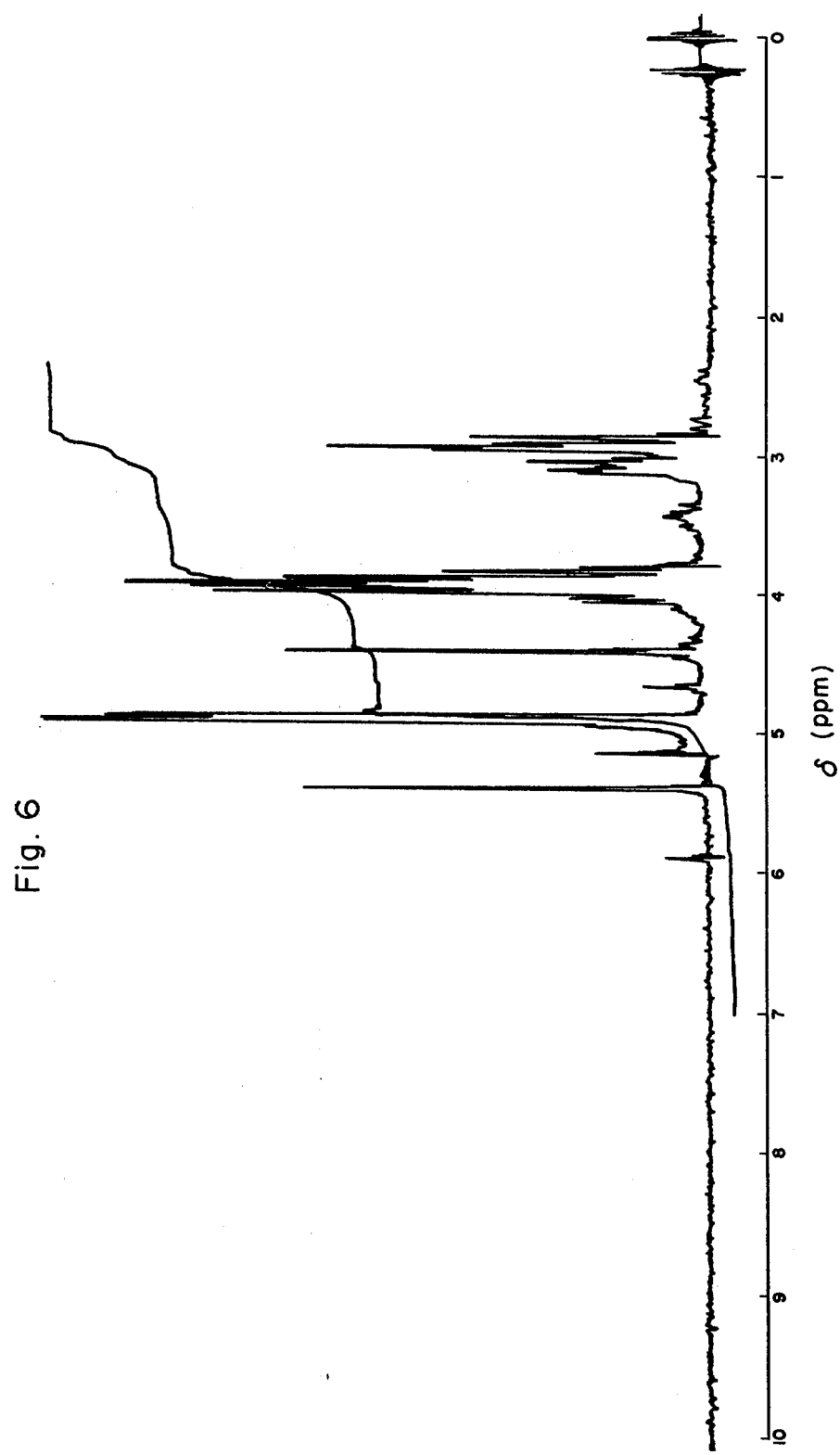
Figure 7:
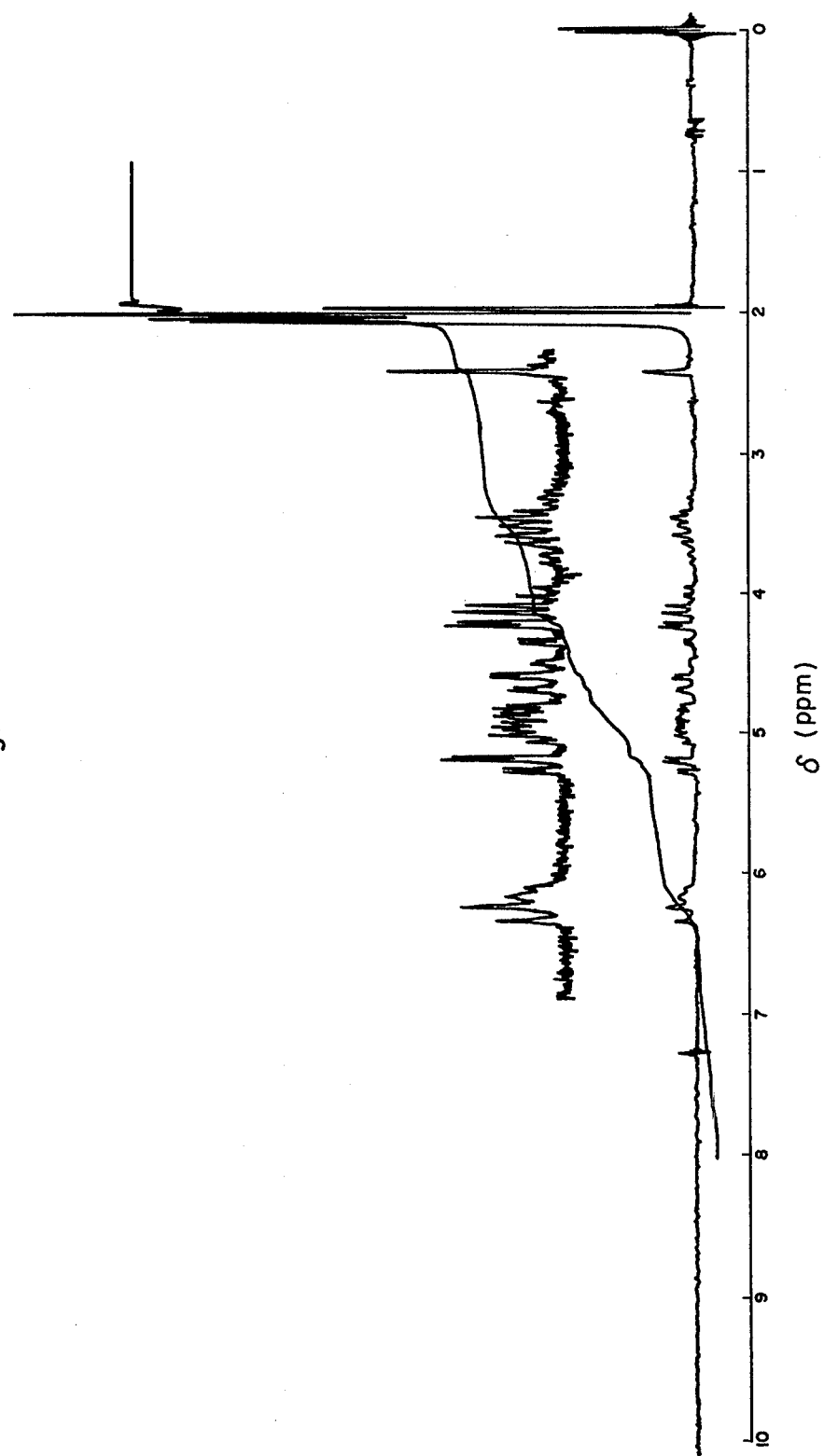
Figure 8:
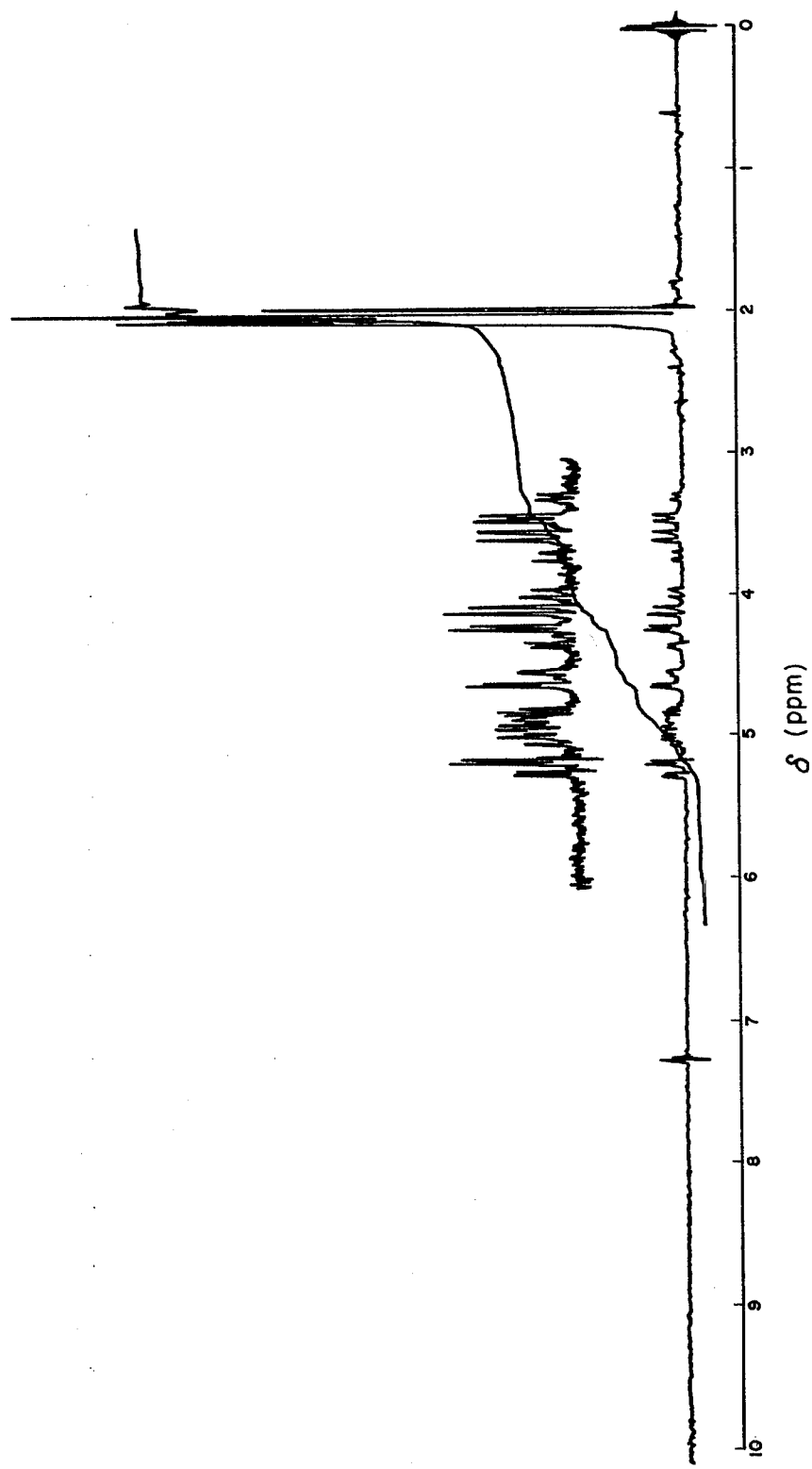
Figure 11:
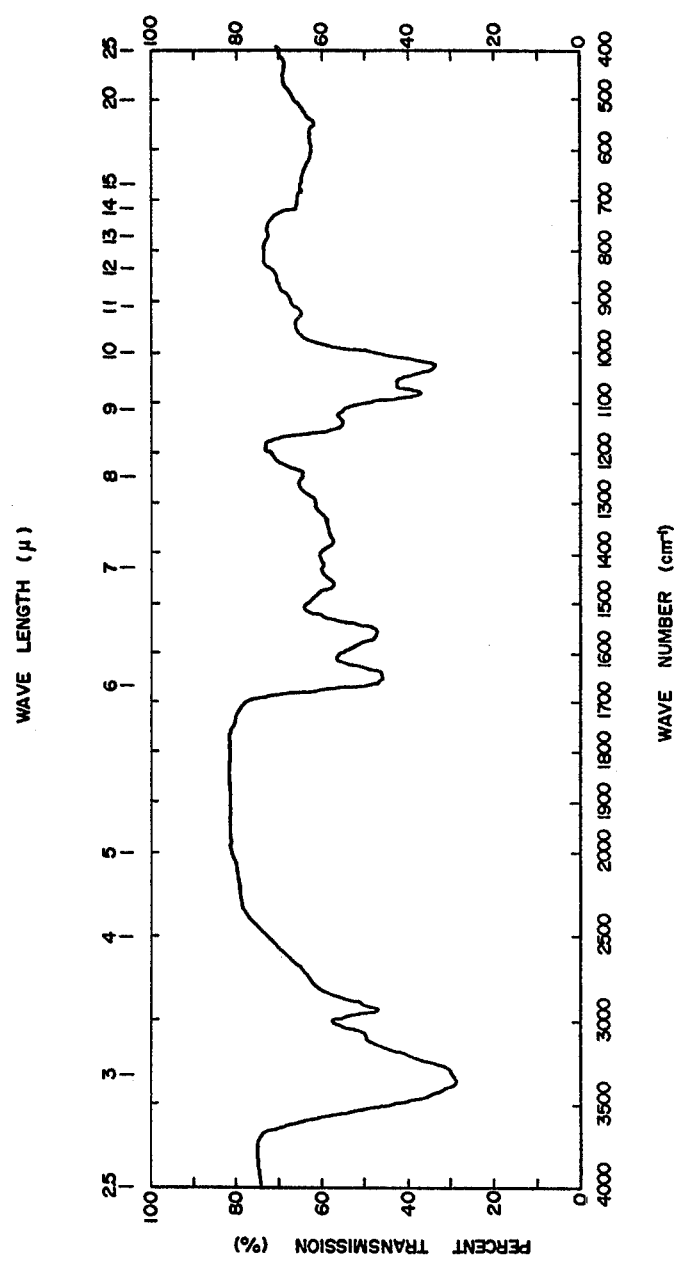

FIGS. 1 to 12 referred to above show the following:
FIG. 1 shows the infrared absorption spectrum (KBr) of P-2563 (I) hydrochloride:
FIG. 2 shows the infrared absorption spectrum (KBr) of P-2563 (II);
FIG. 3 shows the infrared absorption spectrum (KBr) of 'substance P-2563 (I) $f_2$';
FIG. 4 shows the nuclear magnetic resonance spectrum (in D₂O) of P-2563 (I) hydrochloride;
FIG. 5 shows the nuclear magnetic resonance spectrum (in D₂O): of P-2563 (II);
FIG. 6 shows the nuclear magnetic resonance spectrum (in D₂O) of 'substance P-2563 (I) $f_2$';
FIG. 7 shows the nuclear magnetic resonance spectrum (in CDCl₃) of 'substance P-2563 (I) $f_2$'. hexaacetate;
FIG. 8 shows the nuclear magnetic resonance spectrum (in CDCl₃ and D₂O) of 'substance P-2563 (I) $f_2$'.-hexaacetate.
FIg. 9 shows the infrared absorption spectrum (KBr) of P-2563 (III);
FIG. 10 shows the nuclear magnetic resonance spectrum (in D₂O) of P-2563 (III).
FIG. 11 shows the infrared absorption spectrum (KBr) of P-2563 (I) free form.
FIG. 12 shows the nuclear resonance spectrum (in D₂O) of P-2563 (I) free form.

What we claim is:

1. A method for producing antibiotic P-2563 having the formula:

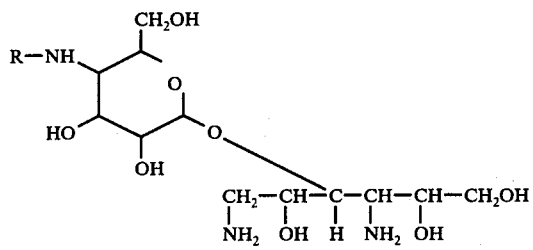

wherein R represents hydrogen or an acyl group, which comprises: cultivating a strain of *Pseudomonas fluorescens* P-2563 (ATCC-31125) in a culture medium contaning assimilable and digestable nitrogen sources until said antibiotic is substantially accumulated therein and recovering the thus accumulated antibiotic.

2. A method according to claim 1, wherein the acyl group has 1 to 7 carbon atoms.

3. A method according to claim 1, wherein the acyl group is selected from the group consisting of formyl, acetyl, propionyl, butyryl, isobutyryl, valeryl, isovaleryl, hexanoyl and heptanoyl.

4. A method according to claim 1, wherein the acyl group has 1 to 5 carbon atoms.

5. A method according to claim 1, wherein the acyl group is selected from the group consisting of formyl, acetyl, propionyl, butyryl, isobutyryl, valeryl and isovaleryl.

* * * * *